(12) United States Patent
Schwaibold

(10) Patent No.: US 11,815,866 B2
(45) Date of Patent: Nov. 14, 2023

(54) VENTILATOR COMPRISING A DEVICE FOR CONTACTLESS DETECTION OF OPERATIONS CARRIED OUT BY A USER

(71) Applicant: Loewenstein Medical Technology S.A., Luxembourg (LU)

(72) Inventor: Matthias Schwaibold, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 15 days.

(21) Appl. No.: 16/222,400

(22) Filed: Dec. 17, 2018

(65) Prior Publication Data

US 2019/0187645 A1   Jun. 20, 2019

(30) Foreign Application Priority Data

Dec. 18, 2017   (DE) .......................... 102017011690

(51) Int. Cl.
*G05B 19/042*    (2006.01)
*A61M 16/00*    (2006.01)
(Continued)

(52) U.S. Cl.
CPC ......... *G05B 19/042* (2013.01); *A61M 16/022* (2017.08); *A61M 16/024* (2017.08); *G06F 3/011* (2013.01); *G06F 3/017* (2013.01); *G06F 3/04815* (2013.01); *G06F 3/167* (2013.01); *G16H 40/63* (2018.01); *A61M 16/0066* (2013.01); *A61M 16/06* (2013.01); *A61M 16/0858* (2014.02); *A61M 2016/0027* (2013.01); *A61M 2016/0033* (2013.01); *A61M 2205/3306* (2013.01); *A61M 2205/3313* (2013.01); *A61M 2205/3331* (2013.01); *A61M 2205/3592* (2013.01); *A61M 2205/50* (2013.01); *A61M 2205/502* (2013.01); *A61M 2205/505* (2013.01); *A61M 2205/507* (2013.01); *A61M 2205/52* (2013.01); *A61M 2205/581* (2013.01); *A61M 2205/583* (2013.01); *A61M 2205/587* (2013.01);
(Continued)

(58) Field of Classification Search
CPC .......... G06F 3/017; G06F 3/167; G06F 3/011; A61M 16/06
See application file for complete search history.

(56) References Cited

U.S. PATENT DOCUMENTS 10,925,551 B2 *   2/2021   Hays ..................... A61M 5/142
2005/0235993 A1 *   10/2005   Baecke ............... A61M 16/024
                                                        128/204.23
(Continued)

FOREIGN PATENT DOCUMENTS

WO    2008042219 A2    4/2008
WO    2017089910 A1    6/2017

*Primary Examiner* — Mohammad Ali
*Assistant Examiner* — Vincent W Chang
(74) *Attorney, Agent, or Firm* — Abel Schillinger, LLP

(57) ABSTRACT

The invention relates to an apparatus and a method for controlling a ventilator by means of a detection unit for control commands, wherein the detection unit detects control commands of a user in a detection region of the detection unit, the detection unit comprising at least one sensor for control commands, a memory, an apparatus for producing digital control commands and an interface for coupling to the ventilator and for transmitting the control commands to the ventilator.

19 Claims, 2 Drawing Sheets

(51) Int. Cl.
    *G16H 40/63*     (2018.01)
    *G06F 3/01*     (2006.01)
    *G06F 3/04815*     (2022.01)
    *G06F 3/16*     (2006.01)
    *A61M 16/06*     (2006.01)
    *G16H 20/40*     (2018.01)
    *A61M 16/08*     (2006.01)
    *G06T 7/20*     (2017.01)

(52) U.S. Cl.
    CPC . *A61M 2205/80* (2013.01); *G05B 2219/2614* (2013.01); *G06T 7/20* (2013.01); *G06T 2207/10012* (2013.01); *G06T 2207/10028* (2013.01); *G06T 2207/10048* (2013.01); *G06T 2207/30196* (2013.01); *G16H 20/40* (2018.01)

(56) References Cited

U.S. PATENT DOCUMENTS

| | | | |
|---|---|---|---|
| 2007/0023044 A1 | 2/2007 | Kwok | |
| 2007/0193582 A1 | 8/2007 | Kwok | |
| 2011/0261051 A1* | 10/2011 | Meyer | G09G 3/32 345/419 |
| 2012/0075290 A1* | 3/2012 | Kurosaki | H04N 13/183 345/419 |
| 2013/0253733 A1* | 9/2013 | Lee | B64C 39/024 701/2 |
| 2016/0257000 A1* | 9/2016 | Guerin | B25J 9/1671 |
| 2016/0364088 A1* | 12/2016 | Bejot | G06F 3/04842 |
| 2017/0139548 A1* | 5/2017 | De Las Heras | G06F 40/134 |
| 2018/0329504 A1 | 11/2018 | Zivaknejad | |
| 2018/0365887 A1* | 12/2018 | Wang | G06T 17/00 |

\* cited by examiner

VENTILATOR COMPRISING A DEVICE FOR CONTACTLESS DETECTION OF OPERATIONS CARRIED OUT BY A USER

CROSS-REFERENCE TO RELATED APPLICATIONS

The present application claims priority under 35 U.S.C. § 119 of German Patent Application No. 102017011690, filed Dec. 18, 2017, the entire disclosure of which is expressly incorporated by reference herein.

BACKGROUND OF THE INVENTION

1. Field of the Invention

The invention relates to ventilator comprising a device for the contactless detection (capture) of analog operating processes, in particular, of a user.

2. Discussion of Background Information

Ventilators according to the prior art comprise a display apparatus on the appliance, said display apparatus typically consisting of a two-dimensional display, often a graphical display, and operating elements in the form of buttons, turn-and-push buttons, sliders or touchscreen areas.

A disadvantage of the prior art is that the amount of information to be detected at the same time cannot be prepared in optimal fashion for the human perception. Moreover, in the case of an access via at least one interface, it is only possible to resort to the operating elements of the computer or the like.

The interaction of the user with the above-described display units is becoming ever more complex, as a result of which intelligent and/or intuitive operating concepts are required.

In view of the foregoing, it would be advantageous to have available an apparatus that is improved over the prior art and an improved method for detecting contactless operating processes of a user.

SUMMARY OF THE INVENTION

The present invention provides an apparatus for controlling a ventilator by means of a detection unit for control commands, wherein the detection unit detects control commands of a user in a detection region of the detection unit, wherein the detection unit comprises at least one sensor for control commands, a memory, an apparatus for producing digital control commands and an interface for coupling to the ventilator and for transmitting the control commands to the ventilator.

The apparatus may further be characterized in that the ventilator comprises an interface for transmitting data to the detection unit.

The apparatus may further be characterized in that the detection unit is embodied as a camera.

The apparatus is also characterized in that the detection unit is embodied as a 3D camera or a TOF camera with a detection region.

The apparatus may further be characterized in that the detection unit is embodied to process and evaluate image data or gestures detected in the detection region.

The apparatus may further be characterized in that the detection unit compares current image data with predetermined image data for the purposes of evaluating the movement or gesture of a user, wherein the predetermined image data is stored in the memory.

The apparatus may further be characterized in that at least one application, an interaction and/or a control of different functions of the ventilator is/are activatable or deactivatable on the basis of the gesture detected in the detection region.

The apparatus may further be characterized in that the detection unit is coupled to an illumination unit for illuminating the detection region.

The apparatus may further be characterized in that the illumination unit emits light in the visible range and/or in the infrared spectral range.

The apparatus may further be characterized in that the illumination unit projects a virtual operating element into the detection region.

The apparatus may further be characterized in that the illumination unit projects a virtual image of display and/or operating elements of the ventilator into the detection region.

The apparatus may further be characterized in that the illumination unit projects a virtual image of the ventilator into the detection region.

The apparatus may further be characterized in that the illumination unit (32) projects measurement values or evaluations (36) of the ventilator into the detection region (24).

The apparatus may further be characterized in that the detection unit (22) is arranged in or on the ventilator (20).

The apparatus may further be characterized in that the detection unit (22) is embodied as a remote control.

The apparatus may further be characterized in that the illumination unit (32) is arranged in or on the detection unit (22) or the ventilator (20).

The apparatus may further be characterized in that the detection unit comprises a speech sensor (25) and identifies voice commands (23) and converts said voice commands into digital control commands and transmits said voice commands to the ventilator (18, 20) via the interface (28), wherein the detection unit (22) is embodied to authenticate (30) voice commands (23) and generates an optical and/or auditory and/or graphical response for the user before the control command is implemented.

The present invention further provides a method for controlling a ventilator (20) by means of a detection unit (22) for control commands, wherein the detection unit (22) detects control commands (23) of a user in a detection region (24) of the detection unit (22), wherein the detection unit (22) comprises at least one sensor (25) for control commands (23), a memory (29), an apparatus (27) for producing digital control commands and an interface (28) for coupling to the ventilator and for transmitting the control commands to the ventilator (20).

The present invention further provides an apparatus for controlling a ventilator by means of a detection unit for control commands, wherein the detection unit detects analog control commands of a user in a detection region of the detection unit, wherein the detection unit comprises at least one sensor for analog control commands, a memory, a low-pass filter and/or a high-pass filter, and A/D converter for producing digital control commands and an interface for coupling to the ventilator and for transmitting the control commands to the ventilator.

If the detection unit detects analog control commands of a user, the sampling frequency of the A/D converter is at least twice as high, for example, as the highest occurring frequency in the sampled signal of the analog control command.

The sleep therapy appliance and/or ventilator according to the invention comprises a virtual, spatially visible (i.e., three dimensionally visible) display unit and/or operating elements, which are not situated directly in the appliance and consequently are also readable and operable from a distance.

The display unit and/or operating elements are visualized by a suitable imaging unit, for example 3D glasses, semi-transparent 3D glasses, a contact lens that produces spatial images, a monitor with 3D functionality (for example, with shutter glasses or polarization glasses) or a projection device with a 3D functionality. The imaging unit produces a spatial perception of information for at least one observer.

Either the imaging unit can be connected directly to the ventilator or the imaging unit and the ventilator are both connected to an image production unit, which produces the spatial images from the data of the ventilator with a very short time delay, or the imaging unit is connected to the image production unit, which produces spatial images from previously received and stored appliance data. The imaging unit and image production unit may be situated in the same housing.

The communication between ventilator and image production unit, and between image production unit and imaging unit, is implemented by electrical signals or electromagnetic waves or a light guide. Possible communications channels may be: The Internet, a LAN, mobile radio, LPWA, a USB, a serial interface, VGA, HDMI, DisplayPort, Bluetooth, etc.

In addition to the optical information item, an acoustic information item is preferably also produced, in particular alarm sounds, human speech, speech of an artificial voice, music or acoustic feedback when operating a virtual operating unit, for example latching sounds in the case of a virtual rotate-and-push button. As a result of the optical and acoustic output, the user is situated in a virtual reality together with the ventilator.

By way of example, the detection region is the surroundings of the user, i.e., the action space of their hands and legs. However, imaging need not be implemented precisely in this region. In the case of 3D glasses, the image is produced directly in front of the eyes. In the case of a projection onto a screen, the detection region is distant from the action space of the user. According to the invention, the detection region is therefore the sum of the imaging region (e.g., 3D glasses or screen) and action space in at least some cases.

The present invention further provides an apparatus for controlling a ventilator by means of a detection unit for control commands, wherein the detection unit detects control commands of a user in a detection region of the detection unit, wherein the detection unit comprises at least one sensor for control commands, a memory, an apparatus for producing digital control commands and an interface for coupling to the ventilator and for transmitting the control commands to the ventilator, wherein the detection unit is embodied for processing and evaluating image data or gestures detected in the detection region and is embodied as a camera.

The present invention further provides an apparatus for controlling a ventilator by means of a detection unit for control commands, wherein the detection unit detects control commands of a user in a detection region of the detection unit, wherein the detection unit comprises at least one sensor for control commands, a memory, an apparatus for producing digital control commands and an interface for coupling to the ventilator and for transmitting the control commands to the ventilator, wherein the illumination unit projects a virtual image and measurement values or evaluations of the ventilator into the detection region.

BRIEF DESCRIPTION OF THE DRAWINGS

Further benefits and features of the present invention will emerge from the description of the exemplary embodiments, which will be explained with reference to the accompanying drawings.

In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
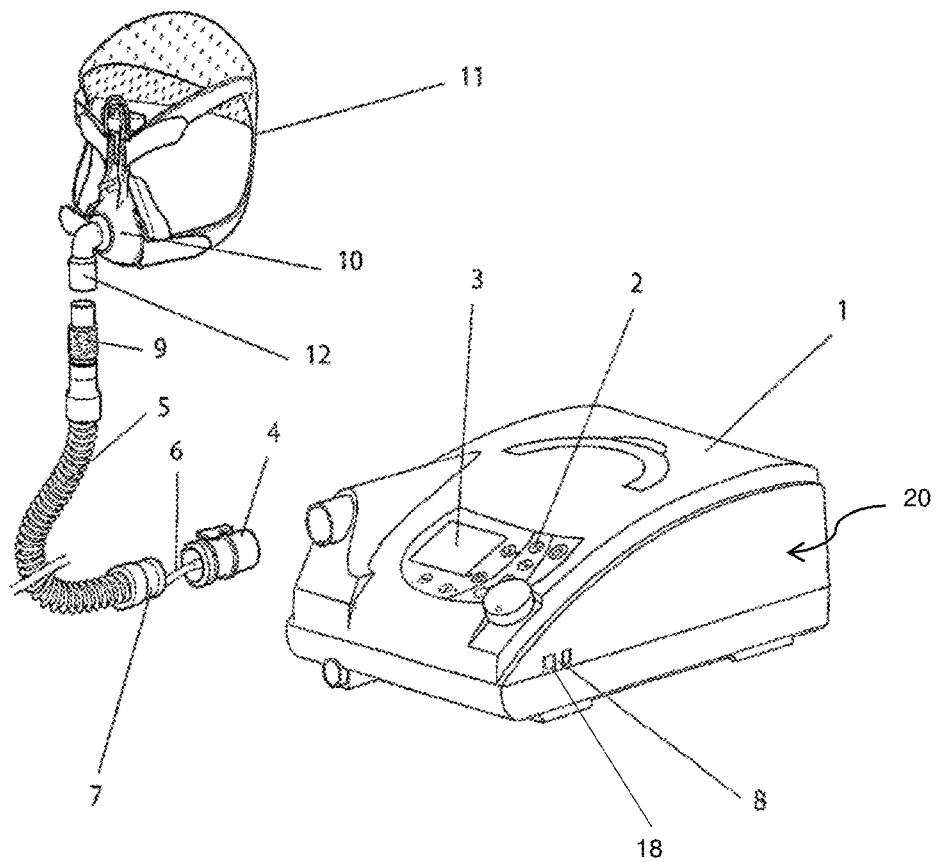
FIG. 1 shows the basic setup of an apparatus for ventilation.

FIG. 1 shows the basic setup of an apparatus for ventilation. In the region of an appliance housing (1) of the ventilator (20), which has a respiratory gas source in the appliance interior, there are arranged an operating element (2) and an operation and information system (3) consisting of a display, a touch-sensitive input unit with at least one control panel. A connecting tube (5) is connected by way of a coupling (4). An additional pressure measuring tube (6) can extend along the connecting tube (5), said pressure measuring tube being connectable to the appliance housing (1) by way of a pressure input nozzle (7). In order to enable data transfer, the appliance housing (1) has at least one interface (8, 18). Moreover, a humidifier can be adapted.

An expiratory element (9) is arranged in the region of an extension of the connecting tube (5) distant from the appliance housing (1). An expiratory valve can likewise be used.

The ventilator (20) can be used as a sleep-therapy appliance, as a humidifier or nebulizer, as a high-flow appliance, as an anesthesia appliance, as a clinical ventilator or home ventilator or emergency ventilator.

FIG. 1 moreover shows a patient interface, which is embodied as a ventilation mask (10) and implemented as nasal mask. Attachment in the region of the head of a patient can be brought about by way of headgear (11). In the region of the extent thereof facing the connecting tube (5), the patient interface (10) has a coupling element (12).

Data, such as e.g. dead space volume, can be input and/or output by way of the interface (8, 18). The interfaces can be implemented in a manner connected by wires, as an infrared interface, as a Bluetooth interface or as a USB. Preferably, provision is also made for a card slot. The interface (8) can also be embodied as a LAN interface or any other interface for connection to the Internet. In the region of an appliance housing, an oxygen connection valve can be adapted to the apparatus for ventilation. It is conceivable to additionally enrich the respiratory gas with oxygen so as to improve the patient care.

By way of the interface (8)—for example embodied as a card slot or USB—it is also possible for data external to the therapy to be loaded into the ventilator according to the invention or to be executed thereby. The user must confirm a query in the operating field—if the appliance identifies external storage media—whereupon the data are selectively stored in the region of the ventilator or executed.

The ventilator (20) according to the invention is designed in such a way that it can be connected to a patient by way of a tube and a patient interface so as to provide ventilation. It comprises a source for respiratory gas, which, for example, is embodied as an electric motor with an impeller, and a device for establishing pressure and/or flow and/or volume of the respiratory gas, and also a control unit, which is configured in such a way that it determines, for each respiratory cycle, a respiratory gas pressure on the basis of a predetermined value for the patient and/or on the basis of measurement signals for the pressure and/or flow and/or volume parameters, and regulates the source for respiratory gas in such a way that the respiratory gas pressure is generated.

The control unit is furthermore configured in such a way that it determines the current pressure and/or flow and/or the volume of respiratory gas and displays the current value by way of the operation and information system (3) connected to the control unit. The control unit is moreover configured in such a way that it determines changes in the trend of its calculations in relation to one or more parameters over time, wherein the changes in the trend can be displayed on the display.

Furthermore, the control unit compares those parameter values which have been predetermined by a user, e.g. upper and lower pressure limits or a maximum tolerable number of apneas per unit time, or a maximum tolerable leakage, with the current values and generates user information in relation to deviations from the specification. The user information is preferably visualized graphically by way of the operation and information system (3).

Figure 2:
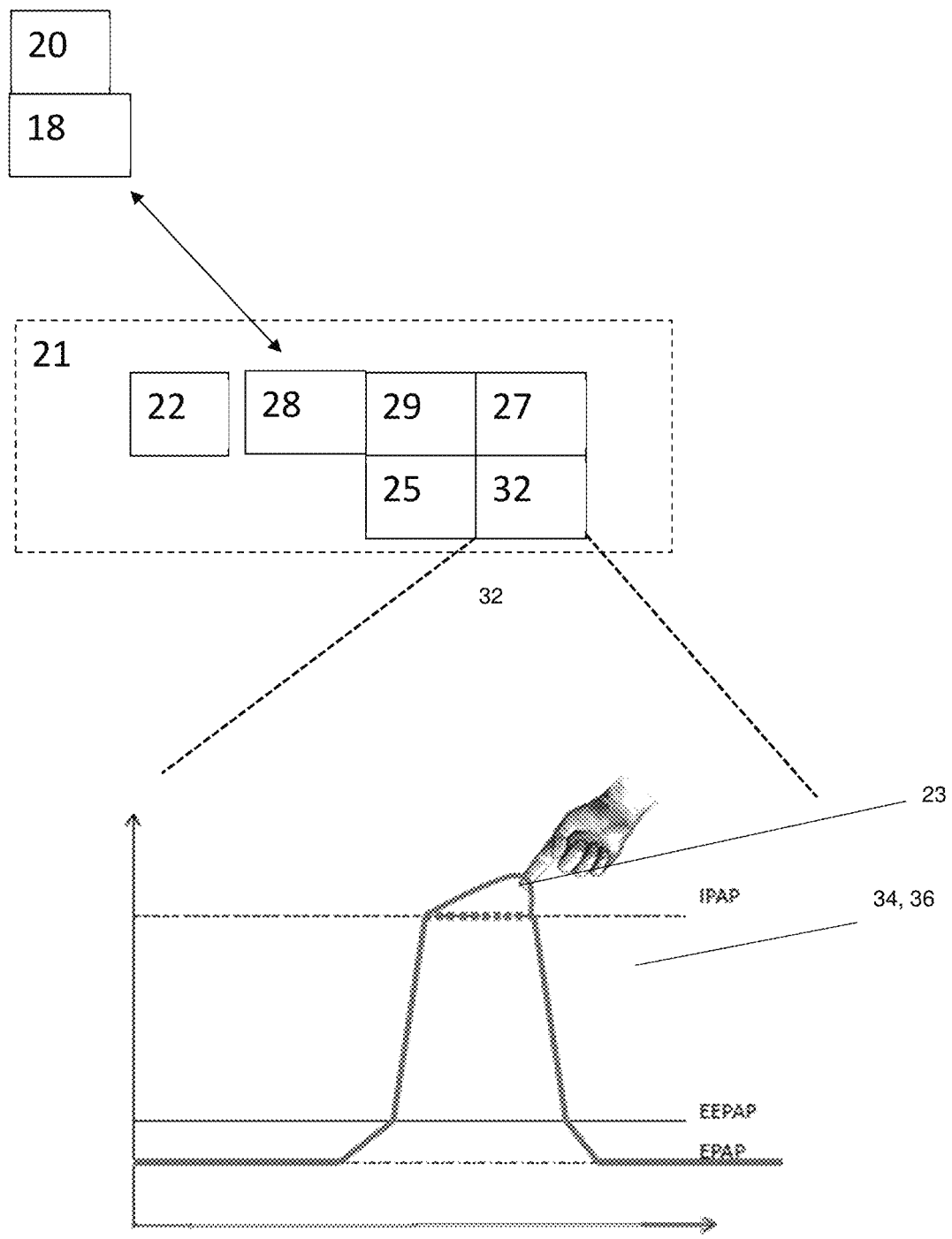
FIG. 2 schematically shows the interaction between ventilator and the control apparatus.

FIG. 2 schematically shows the interaction between ventilator and the control apparatus. The apparatus (21) for controlling the ventilator (20) detects control commands (23) of a user in a detection region of the detection unit (22) by means of the detection unit (22) for control commands. To this end, the detection unit (22) comprises at least one sensor (25) for control commands (23), a memory (29), an apparatus (27) for producing digital control commands and an interface (28) for coupling to the ventilator and for transmitting the control commands to the ventilator (20).

The ventilator comprises a corresponding interface (18) to the detection unit (22). By way of example, the interfaces transmit data two ways. By way of example, the interfaces use Bluetooth or other radio transmission methods.

The detection unit (22) is coupled to an illumination unit (32) for illuminating the detection region, or it comprises the latter. The illumination unit (32) emits light in the visible range and/or in the infrared spectral range. The illumination unit (32) projects a virtual operating element and/or a virtual image of display and/or operating elements (34) into the detection region.

The detection unit (22) is embodied to process and evaluate image data or gestures (23) detected in the detection region. By way of example, for the purposes of identifying gestures, the detection unit (22) compares current image data with predetermined image data for the purposes of evaluating the movement or gesture (23) of a user, wherein the predetermined image data is stored in the memory (29).

At least one application, an interaction and/or a control of different functions of the ventilator (20) is activated or deactivated on the basis of the gesture (23) detected in the detection region. In the present case, the user sets the IPAP pressure by a wiping gesture.

Advantageously, an article and/or a user and/or gestures carried out by the latter and/or operating processes are detectable in three dimensions by means of the detection unit. By way of example, movement of a hand or of a finger is consequently detected in three dimensions; this corresponds to a virtual actuation of a function of the ventilator, for example. Here, this may relate to the detection of an operating process using a gesture, such as a back-and-forth movement of a finger or a wiping movement or an opening of the hand as a zoom movement, for example.

The detection unit converts the detected gesture or movement into a corresponding electrical signal and transmits the latter to the ventilator, which assigns the information item, which is accordingly contained in the electrical signal, to the desired operating process.

In one embodiment, the ventilator or sleep-therapy appliance is presented by the imaging unit in a twin image of its form and with its display and operating elements, just like the real ventilator, in order to offer the user the same information items and/or action possibilities as if they were situated within sight and/or within reach of the appliance.

In a preferred embodiment, the measurement values, the other information items from the appliance and/or about the patient and the operating elements are presented in extended form as an addition to, or instead of, the faithful image in order to present to the user the perception of the information item and the action possibilities in three dimensions and in optimized fashion, as would not be possible on the appliance with the two-dimensional display thereof.

The display elements are distinguished by virtue of certain particularly relevant information items being presented not only in magnified fashion but also spatially in front of or over less relevant information items. Here, a display logic makes a decision relating to the relevance of the display elements in the respective current context.

Here, in the case of at least one peculiar and/or critical pattern in the respiratory flow of the patient, as identified by the ventilator or the image production unit, a respiratory flow signal is presented spatially in front of at least one other signal, for example the pressure signal or the leakage signal. Here, the respiratory flow signal itself can be presented either in two dimensions (e.g., a flat curve) or in three dimensions (e.g., a curve with a thickness, width and depth).

Preferably, in the case of at least one peculiar and/or critical pattern in the leakage curve of the mask or of the patient, a leakage signal is presented spatially in front of at least one other signal, for example the pressure signal or volume signal. Here, the leakage signal itself can be presented either in two dimensions (e.g., a flat curve) or in three dimensions (e.g., a curve with a thickness, width and depth).

Preferably, a time curve of more than one minute is presented for at least one presented signal in such a way that the newest time interval is situated in front of the older time intervals of the signal. If the presentation of the foremost time interval is completely filled, the latter is offset to the back by at least a perceivable distance, and the current values of the signal are presented spatially in front thereof in a new time interval.

Preferred signals, which are presented arranged spatially in relation to one another, are: respiratory flow of the patient, leakage, therapy pressure, respiratory volume, respiratory frequency, time duration of inspiration, time duration of expiration, ratio of time durations to one another, oxygen saturation in the blood, $CO_2$ concentration in the blood, $CO_2$ concentration in the respiratory flow, $O_2$ concentration in the respiratory flow, pulse rate, pulse signal, pulse wave signal, trigger signal, type of breath, expected respiratory volume, respiratory contour, resistance of the airways, respiratory exertion, respiratory excursion, breathing/snoring noises, respiratory events (e.g., apnea), temperature, humidity, use times and durations of the ventilator, settings of the ventilator or accessories. The signals are presented as curves, as current numerical value, as spatial marking, as numerical value curve, as a bar graph, as a column graph, as a pie chart or as a radar chart. Here, it is possible to present either current data or data from the past, which are stored, for example, in the ventilator or in the image production unit or on a data storage medium or on a server.

Numerical values can be presented in three dimensions in a spatial table, in which the size of the value or its position (front/back, top/bottom) or its color contain an interpretation. By way of example, all values situated above the normal range can be presented above a normal position when seen in space. Values situated below the normal range can be presented below a normal position when seen in space.

Preferably, an additional explanatory information item is presented spatially in relevant situations, in which an action of the user is possible and/or advantageous. This additional explanatory information item typically consists of text or numbers or symbols. Particularly preferably, a link is established between the additional information item and the signals in which the relevant situations were identified.

In one embodiment, there is a spatial relationship between text reading "High leakage" and the leakage signal if elevated leakage is identified and the text is linked to the signal by way of an arrow.

In one embodiment, there is a spatial relationship between text reading "Low saturation" and the $SpO_2$ signal if a low oxygen saturation is identified and the text is linked to the signal by way of an arrow.

In one embodiment, there is a spatial relationship between text reading "Low volume" and the volume or respiratory flow signal if a low respiratory volume or apnea is identified and the text is linked to the signal by way of an arrow.

Further relevant situations may include: disconnection, pressure that is too high, pressure that is too low, volume that is too large, temperature that is too high, temperature that is too low, an inexpedient composition of the respiratory gas ($CO_2$, $O_2$, humidity, etc.), a specific action (for example, actuating an operating element) by the patient or by at least one user, hypopnea, snoring, change in the blood gases, change in the pulse frequency, change in the heartbeat volume, change in respiratory volume, change that in the respiratory pattern, change in the respiratory frequency, changes in the accessories, for example the humidifier.

In the case of particularly critical situations, the presented explanatory information item is additionally presented in a different color than in the case of less critical situations, for example in orange or red. Additionally, it is possible to optically change the explanatory information item in critical situations; by way of example, it can be presented further to the front, it can be presented in enlarged fashion, it can be allowed to blink, it can be allowed to pulsate, or it can be allowed to move forwards and backwards in cyclical fashion.

The explanatory information item may also originate from additional data sources in this case, said additional data sources not being available in the ventilator and not necessarily being presented with an optical link to the signals from the appliance. By way of example, these may be the name of at least one person, for example the patient, a weight, a body size, a date, a time, information items from the case history, information from the device history or messages from persons other than the current user.

The explanatory information item may also consist of evaluative symbols, for example emoticons or checks or +/− symbols or exclamation marks, which allow the user to quickly assess the presented information item or which are disposed in front of a more detailed information plane. Coloring the background or presenting a background image in virtual surroundings, for example a positively or less positively occupied scene, can also serve to assess the information item.

The explanatory information items may also be recommendations for action. By way of example, these could be certain changes on the ventilator or in its settings or for its accessories or these could relate to contacting a caregiver or servicing staff or a servicing organization. Preferably, contact data for these persons or organizations are displayed within the scope of the explanatory information item.

In an alternative embodiment, the imaging unit is at least partly transparent, and so the physician or patient caregiver, for example, can physically see the patient and the ventilator and additional explanatory information items are superimposed for them.

Additionally, one embodiment provides the option of increasingly switching on the explanatory situation by way of a switch, for example in order to run through a learning mode or a tutorial mode using data especially prepared to this end. By way of example, the learning mode provides the user with explanations as to how certain information items are able to be presented and interpreted. Moreover, possible actions are explained to said user in respect of how they can interact with the presented information item and/or with the virtual and real ventilator. Additionally, learning is checked in a tutorial mode, in which the user must provide the answer to and/or solve problems while there is no direct interaction with the ventilation of a real patient.

Preferably, the image production unit can offer different amounts of information and different forms of presenting information, depending on the user or user type. Particularly preferably, more information items are offered to medical user or patient caregiver than to a patient. The learning and tutorial modes, too, are tailored to the amount of information available to the user in each case.

Additionally, the imaging unit offers the possibility of superimposing human persons in spatial representations. Preferably, this occurs at the same time as representation of signals or other information items from the ventilator. Preferably, a medical expert and patient are superimposed in reciprocal fashion such that they can have a conversation about the current therapy situation as if they were in viewing range of one another.

Additionally, an artificial human person can be superimposed and can provide the user with explanatory information items or talk to the latter. By way of example, this virtual person adopts a trainer function, an assistant function or a warning function. Preferably, the virtual person provides the user with explanations regarding the interpretation of the presented information item and/or their options for action in order to modify the presentation of information or the settings of the real ventilator in its virtual surroundings.

In particular, provision is made for the virtual person to explain certain processes on the appliance, on the humidifier or on the respiratory mask to the user using virtual reality.

Particularly preferably, this relates to coupling, decoupling, filling, emptying and cleaning the humidifier and the correct wear and adjustment of the mask. Here, the image production unit has an information item about the employed appliance type, humidifier type and/or mask type so that the virtual trainer uses the same components as the patient.

According to the invention, provision is made for the user, e.g., the physician or patient, to be able to modify the presentation of information during the use of the imaging unit. By way of example, they can superimpose and remove certain information items, enlarge or reduce these in size, displace these or switch between different forms of presentation, for example a spatial curve presentation and a spatial table. Moreover, they can activate and deactivate certain assistance or explanatory functions, for example the superimposition of texts or a virtual person. Moreover, they can activate and deactivate additional information items, such as, for example, data from the case history, name, age, size or reciprocal imaging of patient and caregiver (virtual visit) or change these in terms of the form or size of the presentation. This also applies to acoustic information items and speech output, which, for example, can be activated and deactivated or modified in terms of its volume, or which can be modified in terms of its type/language. Moreover, provision is made for at least one additional real person to be contacted by an action of the user and preferably be incorporated into the virtual reality, for example a patient caregiver, a patient, relatives, service staff, a physician, a nurse, a physiotherapist, a technician, etc. To this end, a data and/or speech connection is established to this person and they are offered an additional spatial and acoustic, or conventionally two-dimensional, representation of the current information items and operational options that are relevant or available to them.

Typically, the way the information is presented is changed by at least one hand movement of the user, preferably in conjunction with a head movement of the user. In the process, at least one virtual operating element is looked at, and operated by, the user. Alternatively, a real operating element may also be actuated, for example a mouse, a keypad, a joystick, a slider, a rotary controller or a touchscreen, which is connected to, or able to interchange data with, the image production unit. A data glove, which identifies hand and finger movements of the user and preferably is able to provide haptic feedback by actuators, for example the feeling of actuating a slider or a rotary controller, is also a possible operating element. Alternatively, the way the information is presented can also be changed by way of a voice command.

According to the invention, provision is made for the user, e.g., the physician or patient, to be able to change the settings or the state of the ventilator during the use of the imaging unit. In particular, provision is made for the ventilation therapy to be able to be started or stopped, for the power of the humidifier to be able to be changed and for at least one therapy pressure or therapy frequency or a comfort function to be able to be influenced. Moreover, provision is made for at least one trigger function or pressure modification speed or the target value for at least one ventilation function, for example a target volume, to be able to be influenced. Moreover, provision is made for at least one notification or one alarm on the appliance to be able to be acknowledged or terminated. Moreover, provision is made for at least one self-test to be able to be triggered or data transmission to be able to be started, either from the appliance to a remote station (for example, reading therapy or service data) or from a remote station to the appliance (new configuration, update of at least one piece of software executed on the appliance). Moreover, provision is made for a test for measuring the ventilator system (resistance, compliance and/or leakage) to be able to be triggered, for example by driving to certain test pressures in predefined states of the accessory (for example, separate from the patient or completely connected to the patient).

Preferably, the image production unit may offer different options for changing the settings or the state of the ventilator in the process, depending on the user or user type. Particularly preferably, more options for change are offered to a medical user or patient caregiver than to a patient.

Typically, the way settings or the state of the ventilator is changed by at least one hand movement of the user, preferably in conjunction with a head movement of the user. In the process, at least one virtual operating element is looked at, and operated by, the user. Alternatively, a real operating element may also be actuated, for example a mouse, a keypad, a joystick, a slider, a rotary controller or a touchscreen, which is connected to, or able to interchange data with, the image production unit. A data glove, which identifies hand and finger movements of the user and preferably is able to provide haptic feedback by actuators, for example the feeling of actuating a slider or a rotary controller, is also a possible operating element. Alternatively, the way the information is presented can also be changed by way of a voice command.

The smart phone is connected to the appliance by wires or Bluetooth; the physician in the clinic has a "Weinmann Physician App" and can simply order "IPAP to 20" during the patient visit while they keep looking at, and keep at least one hand by, the patient. The app would then convert the voice commands into conventional remote-control commands and transmit these to the appliance.

According to the invention, a speech and/or gesture recognition can be implemented in the cloud (on the Internet). The data of a speech and/or gesture recognition are detected in situ and transmitted to the cloud for evaluation purposes. More computational power is available there and the recognition algorithms can be continuously optimized—better than on local terminals. Thus, the detection unit (22) can consist of a plurality of components, which need not all be situated in situ but which may also be partly situated remotely on a server.

To this end, the detection unit (22) and/or the apparatus (21) for controlling a ventilator have at least one interface for transmitting the data of a voice and/or gesture recognition to a computer system or server. By way of example, the evaluated data are also received again via this interface.

According to the invention, monitoring and acknowledging alarms is also possible by means of the voice and/or gesture recognition, as illustrated. According to the invention, service processes, e.g., the installation of firmware, the transmission of data, the triggering of certain self-tests, is also possible by means of the voice and/or gesture recognition.

This holds true for controller, which is connected to the ventilator and which is able to convert voice commands into control commands. It has a speech sensor, a memory unit, a processing unit, an interface to the appliance, etc. The processing unit contains appropriate safety and plausibility logic units. It also contains an authentication logic unit, with a graphic/speech response to the user.

According to the invention, in the method for contactlessly detecting users and gestures and/or operating processes implemented by the latter, the user and gestures and/or operating processes implemented by the latter are detected in three dimensions by means of an optical detection unit.

What is claimed is:

1. An apparatus for controlling a ventilator by means of a detection unit for control commands, wherein the detection unit is embodied as a 3D camera or a TOF camera with a detection region and detects control commands of a user in the detection region, the detection unit comprising at least one sensor for control commands, a memory, a device for producing digital control commands, and an interface for coupling to the ventilator and for transmitting the control commands to the ventilator, and wherein the detection unit is coupled to an illumination unit for illuminating the detection region, the illumination unit being capable of projecting an item of information spatially in front of or over another item of information and a display logic makes a decision relating to which item of information is presented in front of or over another item of information based on a relevance of an item of information in a current context, wherein the detection unit further comprises a speech sensor and identifies voice commands and converts the voice commands into digital control commands and transmits the voice commands to the ventilator via the interface, the detection unit being configured to authenticate voice commands and generating an optical and/or auditory and/or graphical response for a user before the control command is implemented.

2. The apparatus of claim 1, wherein the items of information which are projected spatially in front of or over another are selected from respiratory flow of a patient, leakage, respiratory volume, respiratory frequency, time duration of inspiration, time duration of expiration, ratio of time durations to one another, oxygen saturation in blood, $CO_2$ concentration in blood, $CO_2$ concentration in respiratory flow, $O_2$ concentration in respiratory flow, pulse signal, pulse wave signal, trigger signal, type of breath, expected respiratory volume, respiratory contour, resistance of airways, respiratory exertion, respiratory excursion, breathing/snoring noises, respiratory events, temperature, humidity, use times and durations of the ventilator, settings of the ventilator or accessories.

3. The apparatus of claim 1, wherein the detection unit compares current image data with predetermined image data for purposes of evaluating movement or gesture of a user, the predetermined image data being stored in the memory.

4. The apparatus of claim 1, wherein at least one application, an interaction and/or a control of different functions of the ventilator is/are deactivatable on the basis of a gesture detected in the detection region.

5. The apparatus of claim 1, wherein the illumination unit emits light in a visible range.

6. The apparatus of claim 1, wherein the illumination unit emits light in an infrared spectral range.

7. The apparatus of claim 1, wherein the illumination unit projects a virtual operating element into the detection region.

8. The apparatus of claim 1, wherein the illumination unit projects a virtual image of display of the ventilator into the detection region.

9. The apparatus of claim 1, wherein the illumination unit projects evaluations of the ventilator into the detection region.

10. The apparatus of claim 1, wherein the items of information are presented as one or more of a curve, spatial marking, numerical value curve, bar graph, column graph, pie chart or radar chart.

11. An apparatus for controlling a ventilator by means of a detection unit for control commands, wherein the detection unit detects control commands of a user in a detection region of the detection unit, the detection unit comprising at least one sensor for control commands, a memory, a device for producing digital control commands, and an interface for coupling to the ventilator and for transmitting the control commands to the ventilator, and wherein the detection unit is coupled to an illumination unit for illuminating the detection region, the illumination unit being capable of projecting an item of information spatially in front of or over another item of information and a display logic makes a decision relating to which item of information is presented in front of or over another item of information based on a relevance of an item of information in a current context, wherein the detection unit further comprises a speech sensor and identifies voice commands and converts the voice commands into digital control commands and transmits the voice commands to the ventilator via the interface, the detection unit being configured to authenticate voice commands and generating an optical and/or auditory and/or graphical response for a user before the control command is implemented.

12. The apparatus of claim 11, wherein the items of information which are projected spatially in front of or over another are selected from respiratory flow of a patient, leakage, respiratory volume, respiratory frequency, time duration of inspiration, time duration of expiration, ratio of time durations to one another, oxygen saturation in blood, $CO_2$ concentration in blood, $CO_2$ concentration in respiratory flow, $O_2$ concentration in respiratory flow, pulse signal, pulse wave signal, trigger signal, type of breath, expected respiratory volume, respiratory contour, resistance of airways, respiratory exertion, respiratory excursion, breathing/snoring noises, respiratory events, temperature, humidity, use times and durations of the ventilator, settings of the ventilator or accessories.

13. The apparatus of claim 11, wherein the items of information are presented as one or more of a curve, numerical value, spatial marking, numerical value curve, bar graph, column graph, pie chart or radar chart.

14. The apparatus of claim 11, wherein the illumination unit emits light in a visible range.

15. The apparatus of claim 11, wherein the illumination unit emits light in an infrared spectral range.

16. The apparatus of claim 11, wherein the illumination unit projects a virtual operating element into the detection region.

17. The apparatus of claim 11, wherein the illumination unit projects a virtual image of display and/or operating elements of the ventilator into the detection region.

18. The apparatus of claim 11, wherein the illumination unit projects a virtual image of the ventilator into the detection region.

19. The apparatus of claim 11, wherein the illumination unit projects measurement values or evaluations of the ventilator into the detection region.

* * * * *